United States Patent [19]

Onillon et al.

[11] 4,109,159

[45] Aug. 22, 1978

[54] METHOD AND AN AUTOMATIC DEVICE FOR ANALYZING VARIATIONS IN THE TRANSPARENCY OF A SAMPLE

[75] Inventors: Michel Onillon, Vert le Grand; Pierre Roche, Maisons-Alfort; Jean Thenard, Versailles, all of France

[73] Assignee: Commissariat a l'Energie Atomique, Paris, France

[21] Appl. No.: 799,935

[22] Filed: May 24, 1977

[30] Foreign Application Priority Data

Jun. 3, 1976 [FR] France .............................. 76 16785

[51] Int. Cl.² ............................................ G01N 21/28
[52] U.S. Cl. .................................... 250/564; 73/64.1; 250/573; 356/39; 356/201
[58] Field of Search ................. 73/64.1; 250/564, 573; 356/39, 201; 128/2 G

[56] References Cited

U.S. PATENT DOCUMENTS 3,606,539  9/1971  Polanyi et al. ................... 250/564 X
3,625,621  12/1971  Fields ............................... 250/564 X
3,923,397  12/1975  Shuck ..................................... 356/39

OTHER PUBLICATIONS

Korn & Korn, Electronic Analog Computers, McGraw-Hill, 2nd Ed., p. 13; 1956.

*Primary Examiner*—Lawrence J. Dahl
*Attorney, Agent, or Firm*—Lane, Aitken, Dunner & Ziems

[57] ABSTRACT

The method consists in generating an electrical signal B which is representative of the time-dependent variations in transparency, in generating a pulse at the initial instant of measurement, in carrying out an initial measurement of the slope of the curve at the beginning of the portion which has a steep slope, in comparing at predetermined instants the measured value of the initial slope with the slope of the curve which is representative of the signal B at these instants, in generating a second pulse when the measured slope becomes significantly different from the initial slope, and in measuring the time interval which elapses between the first and second pulses.

11 Claims, 6 Drawing Figures

METHOD AND AN AUTOMATIC DEVICE FOR ANALYZING VARIATIONS IN THE TRANSPARENCY OF A SAMPLE

This invention relates to a method and to an automatic device for analyzing variations in the transparency of a sample.

In more exact terms, the present invention is intended to permit the analysis of time-dependent variations in transparency of a solution and more precisely to permit determination of a characteristic time interval which elapses between commencement of analysis of said sample and completion of the analysis as defined by a modification of the variation in said transparency as a function of time. Depending on requirements, the variation can be an increase in transparency or a reduction in transparency.

A problem of this nature can arise in particular in the field of medical analysis when it is found necessary to carry out determinations of lysis or coagulation times. A knowledge of the times of lysis of a clot of whole blood or of euglobulins (plasma proteins) as well as the time of coagulation of plasma or whole blood enable the practicing physician to establish a diagnosis of certain diseases.

By way of example, determination of the time of lysis of the euglobulin is carried out as follows : at the outset, the euglobulin solution appears in the form of a clear liquid having the appearance of distilled water. A few cubic centimeters are placed in a test-tube and a predetermined proportion of coagulant is added. There is thus obtained a gel which has a grey color. The transparency of the coagulated euglobulin solution is highly variable from one type of blood to another. The clot which is maintained at a temperature of 37° C liquefies after a variable time interval ranging from 10 minutes to over 8 hours. On liquefaction, the transparency can vary over a very wide range. The samples which have retained a dark appearance after liquefaction can continue to increase in transparency for a long period of time. However, the rate of transparentization slowsdown at the moment of transition from the state of gel to the state of sol. This moment corresponds to completion of lysis. In consequence, at the beginning of the measurement, the transparency exhibits no variation or only very slight variation (this is referredto as the latent period). At the moment of liquefaction, however, there then takes place a rapid increase in transparency, this fast variation being finally followed by a slow variation.

The curves shown in the accompanying FIGS. 1 and 2 give the variation in transparency T which is plotted as ordinates in accordance with an arbitrary unit as a function of time. In FIG. 1, there is shown the first portion of the curve designated by the reference I which corresponds to the latent period with a very slight variation in opacity followed by the zone II of fast variation in transparency and finally by the zone III of slower variation. The lysis time extends between the beginning of zone I and the end of zone II. FIG. 2 represents another possible configuration of the curve of variation in transparency as a function of time and the same portions of curves I, II and III are again shown. In this case, however, there is found in region I a zone corresponding to a first fast increase in variation having the reference IV but of small amplitude which is in fact included in the latent period.

From the optical point of view, that is, from the point of view of transparency, the process of coagulation thus induced occurs as the dual of lysis. In another words, the opacity is first slight and then increases. On the other hand, the development time is much shorter, namely of the order of a few minutes.

Stated differently, the problem to be solved consists in both cases in measuring a time interval which starts at the beginning of the measurement and ends with the period in which a modification occurs in the rate of variation in transparency.

It will in fact be understood that the lysis time or the coagulation time is not characterized at the beginning and at the end of experiments either by well-defined opacities or by a given rate of development.

The present invention is precisely directed to a method and a device for measuring and analyzing variations in transparency of a sample as a function of time which is applicable in particular to the definition of lysis time and coagulation time.

The method for analyzing the time of useful variation in transparency of a sample in which the end of the useful period of said variations is characterized by a variation in slope of the curve which is representative of said transparency as a function of time is distinguished by the fact that said method consists in generating an electrical signal B which is representative of the time-dependent variations of said transparency, in generating a pulse at the initial instant of measurement, in carrying out an initial measurement of the slope of the curve at the beginning of the portion which has a steep slope, in comparing at predetermined instants the measured value of said initial slope with the slope of the curve which is representative of the signal B at said instants, in generating a second pulse when the measured slope becomes significantly different from the initial slope, and in measuring the time interval which elapses between the first and second pulses.

In a preferrred embodiment, the method consists in generating a second variable signal A, in generating a first pulse at the initial instant of measurement, in carrying out a measurement of the slope of the representative curve at the beginning of the high-slope portion of said curve by increasing the signal A by a value N during a time interval $t$ until the signal B becomes equal to the signal A, the time interval $t$ being stored in memory, in comparing said slope defined by the ratio $N/t$ with the slope of the signal B, in generating a second pulse when the slope of the signal B becomes smaller than the ratio $N/t$ and in measuring the time interval which elapses between the first and the second pulse.

Preferably, the signals A and B are generated in digital form and the value N is a number.

In accordance with another distinctive feature of the method, the time comparison is carried out by comparing the numerical value of the signal B with the numerical value of the signal A which is incremented by the number N at each time interval $t$ and a second pulse is emitted when the value of the signal A becomes higher than that of the signal B.

This invention is also concerned with a device for analyzing time-dependent variations in transparency of a sample in which said variations have a high-slope region followed by a low-slope region. The device essentially comprises means for generating a first signal B which is representative of the time-dependent variations of said transparency, means for generating a second signal A which is variable in time from an initial instant $T_O$, means for generating a first pulse at the initial instant $t_o$, means for generating the signal A, said means being provided with means for making said signal representative of the initial slope of the signal B at the beginning of its high-slope region, means for periodically comparing said slope with the slope of the signal B, means for generating a second pulse when the slope of the signal B becomes higher than the initial slope measured, and means for measuring the time interval which elapses between the first and the second pulses.

In a preferred embodiment, the means for illuminating and collecting the light signal are constituted by an electro-luminescent diode which is supplied during finite periods of time, said diode being placed on one side of the sample, and by a phototransistor placed on the other side of the sample and capable of collecting the light signal which has passed through said sample.

In accordance with another distinctive feature, the means for making the signal A representative of the slope of the signal B comprise means for defining an instant $T_1$ corresponding to the beginning of the high-slope region, means for giving the signal A at said instant $T_1$ a value equal to the value $B_1$ of the signal at said instant and for adding a quantity N to said value $B_1$ in order to ensure that the signal A is of higher value than the signal B at said instant, means for detecting the instant $T_2$ at which the signal B becomes equal to the value $B_1 + N$, and means for measuring the time interval $t$ which elapses between the instants $T_1$ and $T_2$, the ratio $N/t$ being intended to give the value of said slope.

A more complete understanding of the invention will in any case be obtained from the following description of one embodiment of the invention which is given by way of example and not in any limiting sense, reference being made to the accompanying drawings, wherein:

FIGS. 1 and 2 which have already been described are plots of curves which illustrate the variation in transparency of the sample at the time of analysis of the lysis time;

Figure 3:
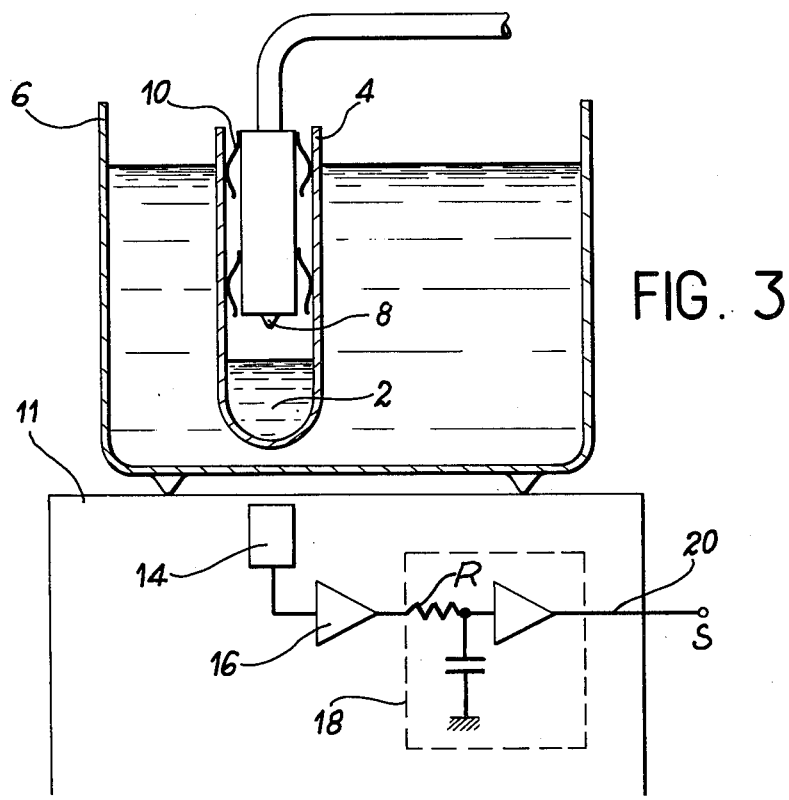
FIG. 3 shows an embodiment of that portion of the device which relative to conversion of optical transparency to an electrical signal.

There is shown in vertical cross-section in FIG. 3 that portion of the device which comprises the sample to be analyzed and serves to convert the optical density of the sample to an electrical signal. The solution 2 of euglobulins or of plasma is placed at the bottom of a test-tube 4. Said test-tube is placed within a tank 6 containing water which is maintained at a temperature of 37° C. The tank 6 is placed on a base 11. Within the test-tube 4 and above the solution 2, there is placed an electroluminescent diode 8 which is maintained with respect to the test-tube by means of centering springs 10, for example. The diode is supplied with electrical pulses, the frequency of which is higher than that of the parasitic light phenomena. A phototransistor 14 is placed beneath the tank 6 and in the line of extension of the test-tube 4. In other words, the electroluminescent diode 8 and the phototransistor 14 are placed on each side of the solution 2 to be analyzed. The output of the phototransistor 14 is connected to an amplifying unit 16 which is associated with an integrating circuit 18 of conventional type. The output 20 of said circuit constitutes the output of the circuit for generating the electrical signal. The time constant of the integrating circuit 18 constituted by the resistor R and the capacitor C has been chosen in such a manner as to ensure that the useful signals are suitably transmitted but that those produced as a result of ambient light phenomena are not transmitted. These variations are mainly those which are caused by daylight (passing of a cloud), opening or closing of windows and those resulting from electric lighting, the frequency of which is of the order of 100 c/s.

In fact, in a preferred embodiment of the device, a number of test-tubes 4 (eight, for example) each containing a solution to be analyzed are placed in the same tank 6. A photodiode 8 and a phototransistor 14 are associated with each test-tube. Light pulses are produced by the electroluminescent diode or diodes 8. These pulses have a time-duration of the order of 50 microseconds. In the case of a device having eight measuring channels, the interval of said pulses is 160 milliseconds. These values are clearly given only by way of example. Thus the amplitude of the light pulses received by the phototransistors is clearly a function of the transparency of the sample and the variations in all the pulses constitute the signal S which is therefore representative of the transparency of the sample at each instant.

Taking account of the fact that the variations of the signal are very slow as mentioned earlier, it would be very difficult to process the signal in the analog form in which it is delivered by the phototransistor. In consequence, the different pulses of the signal S are introduced into an analog-digital converter 30 and this latter delivers at its output a signal B which is identical with the signal S but appears in a digital form.

The signal B thus obtained is transmitted on the one hand to one of the inputs of the comparator 32 and on the other hand to the input of the digital memory 34 through a controlled switch 36. The output of the memory 34 is connected to the second input of digital comparator 32.

The memory 34, or more precisely its contents, in digital form constitutes the signal A and the comparator 32 therefore compares the numerical value of the signal A with the numerical value of the signal B which is applied to its other input. The comparator circuit 32 delivers a signal $F_1$ at its output 38 when A is higher than B and delivers a signal $F_2$ at its output 40 when this is not the case. These two outputs are connected to two outputs of a control logic circuit 42, the design function of which will hereinafter be explained in greater detail. The memory 34 is provided in addition with an input 44 for the incrementation of its contents and an input 46 for the decrementation of its contents. These two inputs 44 and 46 are connected to the output of a pulse generator 48 respectively through the logical gates 50 and 52. The generator 48 delivers N incrementation pulses when a control pulse is applied to its control input 54. The device further comprises a first counter 56 which performs the function of memory and the input of which is connected to the output $S_2$ of the logic circuit 42 through a logical gate 59. Similarly, the circuit comprises a counter 58 mounted for counting-down and connected to the output $S_5$ of the logic circuit 42 through the logical gate 60. In addition, a connection between the counter 56 and the counter 58 makes it possible to transfer the contents of the counter 56 into the counter 58 by means of a control pulse without erasing the contents of the counter 56. The counter 58 which is mounted for counting-down is connected at its output to a zero-crossing detector 62, the output of which is applied on the one hand to the input CH of the logic circuit 42 and on the other hand to the control input 54 of the pulse generator 48. The control input 54 is also connected to the output 40 of the comparator. The circuit further comprises a clock 64 for delivering pulses at a predetermined recurrence frequency, said pulses being applied to the input of the counters 56 and 58 through logical gates 59 and 60.

The circuit also comprises a time-measuring counter 66 which is connected to the output of the clock 70 through the logical gate 68. Said gate is controlled by the state of the output $S_1$ of the logic circuit 42. The circuit further comprises a device 72 for starting-up the installation. By way of example, this device can be designed in the form of a push-button contact which delivers a pulse, on the one hand in order to initiate opening of the switch 36 and which is applied on the other hand to the control input 54 of the pulse generator 48. Finally, the pulse delivered by the contact 72 serves to reset the counters to zero as well as the logic circuit 42.

Figure 4:
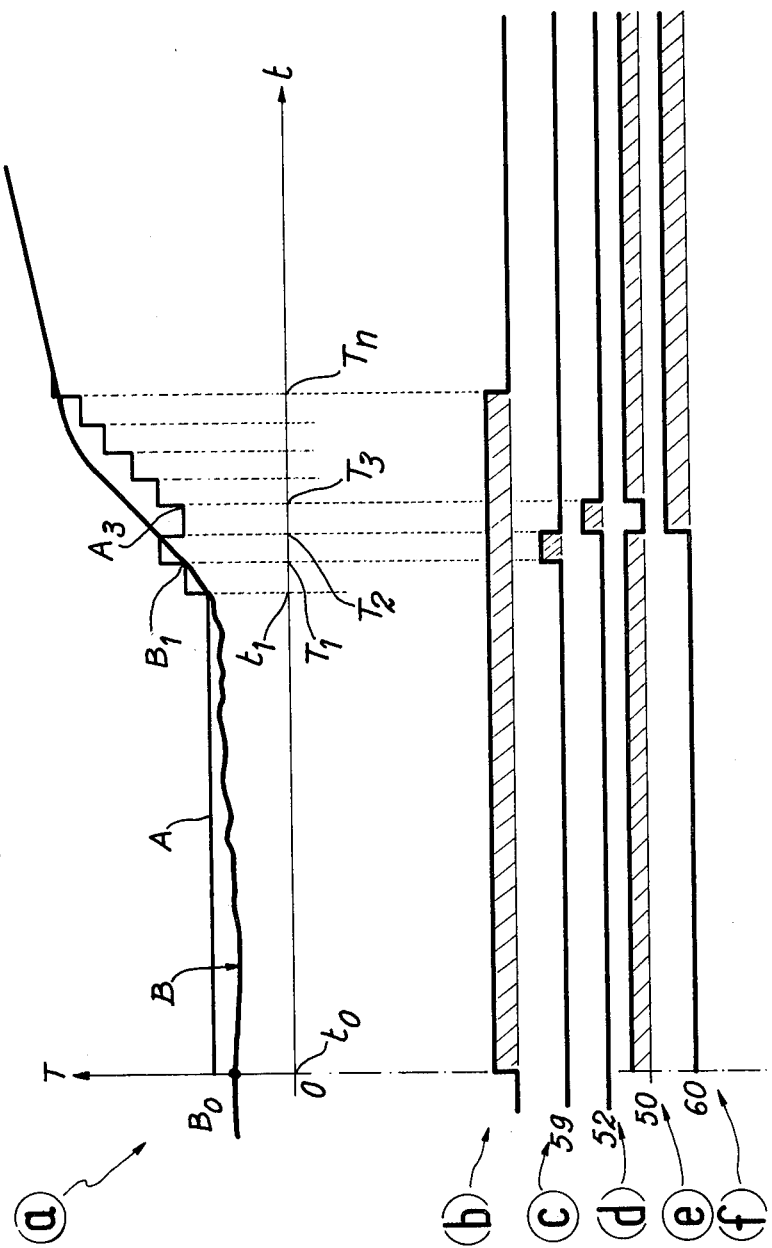
FIG. 4 is a general arrangement diagram of a device for processing said electrical signal in order to determine a lysis time interval.

The operation of the device will become more readily apparent from a study of FIGS. 4. FIG. 4a represents the progressive variation of the signal B as a function of time, that is to say the development of transparency of the sample as a function of time. As stated earlier, the signal B is in fact produced in digital form. In order to provide an easier understanding of FIG. 4a, the signal B has been represented in analog form. The circuit is started-up at the initial instant $t_0$. At this instant, the signal B has a numerical value which is designated as $B_0$ and this numerical value is stored in the memory circuit 48, whereupon the switch 36 is opened. Thus the contents of the memory 34 are no longer influenced by the time-dependent variations of the signal B. This instant $t_0$ constitutes the beginning of the lysis period.

At the instant $t_0$, the contact 72 is therefore depressed, thus delivering a pulse which closes the switch 36 as already mentioned and which also applies a pulse to the control input 54 of the pulse generator 48. In the initial position, the gate 50 is open and the gate 52 is closed. In consequence, the contents of the memory 44 are increased by the value N. A value Ao (Ao = $B_0$ + N) is accordingly obtained in the case of the signal A. Under these conditions, the signal A is of higher value than the signal B and a signal $F_1$ is therefore present at the output 38 of the comparator and applied to the input of the logic circuit 42. A pulse then appears at the output $S_1$ of said logic circuit 42 and opens the gate 68. From this instant $t_0$, the counter 66 therefore receives the pulses delivered by the clock 70.

As time elapses, the signal B varies slowly but remains of lower value than the signal A which remains at its value $B_0$ + N (latent period). At the instant $t_1$, the signal B becomes higher in value than the signal A. As the signal A accordingly becomes lower than the signal B, a pulse $F_2$ is applied on the one hand to the input of the logic circuit 42 and on the other hand to the control input of the pulse generator 48. This pulse has no effect on the logic circuit 42 but causes incrementation of the contents of the memory 34 by the value N (A = $B_0$ + 2N).

When the value of the signal A again becomes lower than that of the signal B (instant $T_1$ of FIG. 4a), a further pulse $S_2$ has the effect on the one hand of producing another incrementation of the contents of the memory 34 by the value N by means of the pulse generator 48. On the other hand, said pulse $S_2$ which is applied to the input of the logic circuit 42 causes the changeover of the output $S_2$ of said circuit which opens the gate 59. The counter 56 can therefore be incremented by the pulse delivered by the clock 64. The signal A then has the value $B_0$ + 3N.

Figure 1:
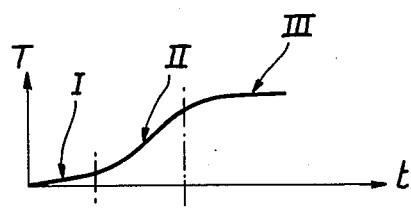

When the signal B again becomes higher in value than the signal A (which occurs at the instant $T_2$), another pulse $F_2$ is applied on the one hand to the pulse generator 48 and on the other hand to the input of the logic circuit 42. This pulse initiates the changeover on the one hand of the output $S_2$ of the logic circuit which closes the gate 59, the changeover of the output $S_5$ which opens the gate 60 and which transfers the contents of the counter 56 into the counter 58 which is wired for counting-down. In addition, the outputs $S_3$ and $S_4$ undergo a reversal of state, thus closing the gate 50 and opening the gate 52. The pulses which are stored in the counter 56 between the instants $T_1$ and $T_2$ represent a time-duration $t$. It is understood that the ratio of the increase of the signal A between the instant $T_1$ and $T_2$ and which has the value N and the time interval $t$ represents the slope of the curve of variation in transparency at the beginning of the fast-variation region (region II of FIG. 1).

Since the gate 52 is open, the contents of the memory 34 are reduced by the number N (decrementation). In this case the signal A therefore has the value $B_0$ + 2N. The pulses delivered by the clock 64 are applied to the input of the gate of the counter 58 since the gate 60 is open. The counter 58 having previously been loaded to the value corresponding to the time interval $t$, the counter 58 is reset to zero when it has received from the clock 64 a number of pulses which also corresponds to said time interval $t$. The instant $t_3$ and the detector for transition to zero of the contents of the counter 58 transmits a pulse to the logic circuit 42 (input CH), then to the pulse generator 48. Under the action of said pulse, the gate 50 is opened and the gate 52 is closed and the contents of the memory 34 are incremented by the value N. The signal A then assumes the value $A_3$ which has in fact the value $B_0$ + 3N.

At the instant $T_3$, there is available on the one hand the value of the slope of the curve in the zone of fast variation in the form of the contents of the counter 56 which contains the equivalent of the time interval $t$. In addition the signal A has the value $A_3$ at this instant, this value being certainly lower than the value of the signal B at this same instant.

Figure 5:
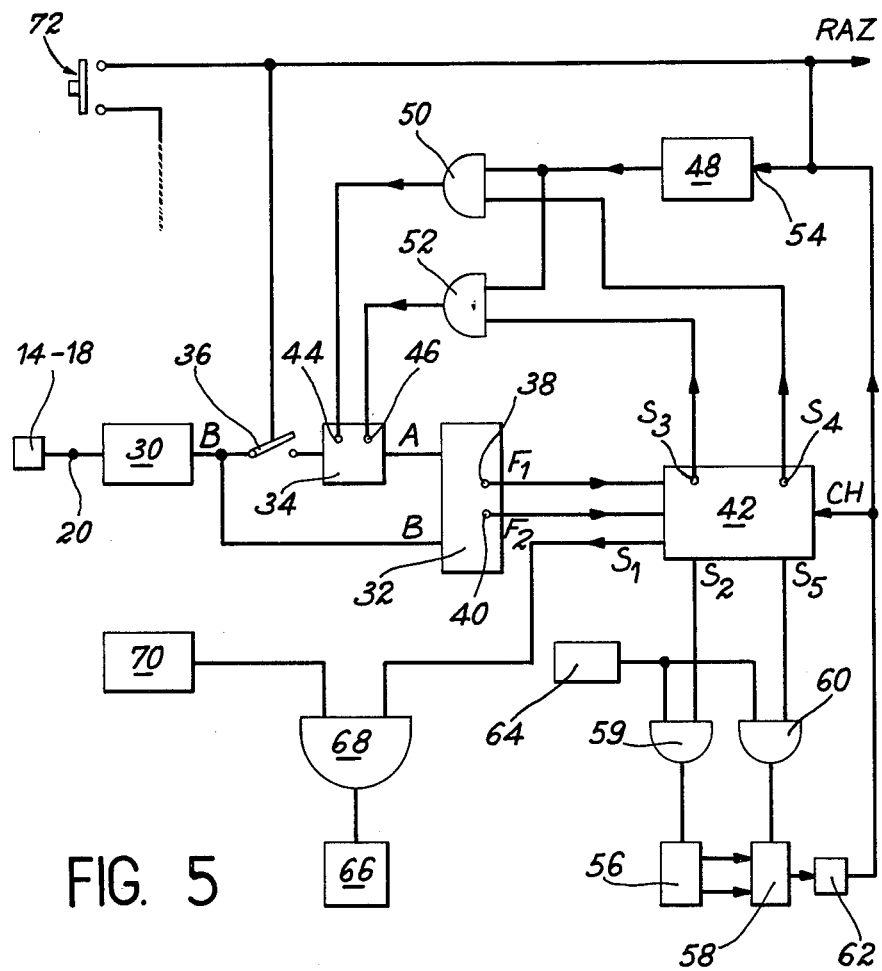
FIG. 5 shows a set of time diagrams which illustrate the operation of the device shown in FIG. 4.

From this instant onwards and starting from the point $A_3$, there take place a series of repetitive operations in which the signal A is given a stair-step waveform, the steps of which have the height N and a width corresponding to the time interval $t$. To this end, the contents of the counter 56 are transferred into the counter 58 at the beginning of each cycle. At the end of the time interval $t$, the counter 58 is reset to zero, thus resulting in the disappearance of a pulse which controls the pulse generator 48. This accordingly results in incrementation of the contents of the memory 34, namely by the signal A. Throughout this period, the signal A remains lower in value than the signal B, which has no effect on the logic circuit 42. At the instant $T_n$ (in FIG. 5, $n = 7$), the signal A becomes higher in value than the signal B. A pulse $F_1$ is applied to the input of the logic circuit 42. The output $S_1$ of said logic circuit changes state, thus closing the gate 68 and stopping the counting by the counter 66 of the pulses delivered by the clock 70. Within the counter 66 there is thus a number of pulses corresponding to the time interval which has elapsed between the instant $t_0$ and the instant $T_n$, that is, precisely the interval which has been defined as the lysis time. It is clearly possible to indicate the contents of the counter 66 in the form of time intervals by multiplying the number of pulses contained by the recurrence frequency of the pulses delivered by the clock 70.

In FIG. 4, the diagrams of the time intervals 4b, 4c . . . 4f represent respectively the state (open or closed) of the logical gates 68, 59, 52, 50 and 60.

As was mentioned earlier, the representative curve is "reversed" when it is desired to measure the coagulation time instead of the lysis time. In order to avoid the need to modify the circuit for this measurement, a complementation circuit is preferably introduced at the output of the converter. This involves the replacement of each bit of the numbers by their complements at the output of the converter.

Figure 2:
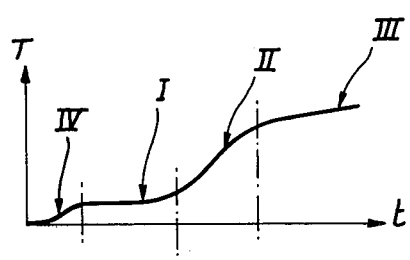

It should be noted in addition that certain "complications" have been introduced into the circuit in order to achieve enhanced reliability and accuracy. For example, determination of the time interval $t$ could have been carried out from the instant $t_1$. It is apparent, however, that by proceeding in this manner (without awaiting the second incrementation) in the case of the curve shown in FIG. 2, the determination of $t$ would be completely erroneous. Similarly, it would have been possible to dispense with the need for decrementation at the instant $T_2$. In this case, however, the signal A would be tangent to the signal B at the instant $t_3$. This would be liable to cause the appearance of the signal for the end of the lysis time whereas this process has not been completed. Decrementation accordingly avoids this danger.

Figure 6:
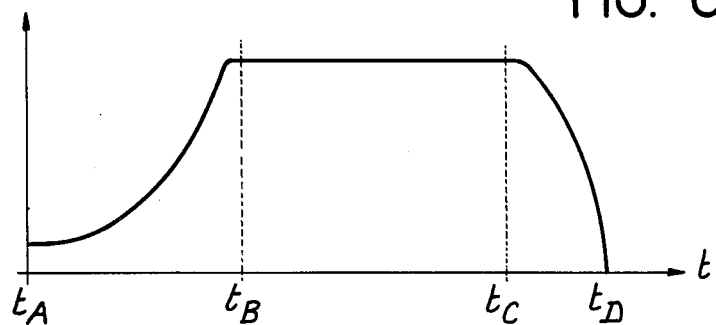
FIG. 6 shows a curve of development of the opacity of a sample in which a bacterial culture is grown and shows that the device in accordance with the invention can also be applied to this particular case of medical analyses.

FIG. 6 gives the variation in optical density of a germ culture in a peptonized medium as a function of time. Between the instants $t_A$ and $t_B$, the curve corresponds to the multiplication of the bacteria. During the period which extends from $t_B$ to $t_C$, there is an equilibrium between increase and death of the cells. Disappearance of all the cells takes place between $t_C$ and $t_C$. This phenomenon can also be studied by means of the device in accordance with the invention.

It is worthy of note that the digital process can be replaced by an identical analog process in the event that the variations in transparency are much too fast.

It will readily be understood that, when making use of an apparatus of this type, the measurement performed will be correct irrespective of the level of the signal B at the beginning and at the end of the phenomenon to be measured (opacity) and irrespective of the duration of the lysis.

What we claim is:

1. A method for analyzing the time of useful variaton in transparency of a sample in which the end of the useful period of said variations is characterized by a variation in slope of the curve which is representative of said transparency as a function of time, wherein said method consists in generating an electrical signal B which is representative of the time-dependent variations of said transparency, in generating a pulse at the initial instant of measurement, in carrying out an initial measurement of the slope of the curve at the beginning of the portion which has a steep slope, in comparing at predetermined instants the measured value of said initial slope with the slope of the curve which is representative of the signal B at said instants, in generating a second pulse when the measured slope becomes significantly different from the initial slope, and in measuring the time interval which elapses between the first and second pulses.

2. A method according to claim 1, wherein said method consists in generating a second variable signal A, in generating a first pulse at the initial instant of measurement, in carrying out a measurement of the slope of the representative curve at the beginning of the high-slope portion of said curve by increasing the signal A by a value N during a time interval $t$ until the signal B becomes equal to the signal A, the time interval $t$ being stored in memory, in comparing said slope defined by the ratio $N/t$ with the slope of the signal B, in generating a second pulse when the slope of the signal B becomes smaller than the ratio $N/t$ and in measuring the time interval which elapses between the first and the second pulse.

3. A method according to claim 2, wherein the signals A and B are generated in digital form and the value N is a number.

4. A method according to claim 3, wherein the time comparison is carried out by comparing the numerical value of the signal B with the numerical value of the signal A which is incremented by the number N at each time interval $t$ and wherein a second pulse is emitted when the value of the signal A becomes higher than that of the signal B.

5. A device for analyzing time-dependent variations in transparency of a sample in which said variations have a high-slope region followed by a low-slope region, wherein said device comprises means for generating a first signal B which is representative of the time-dependent variations of said transparency, means for generating a second signal A which is variable in time from an initial instant $t_0$, means for generating a first pulse at the initial instant $t_0$, means for generating the signal A, said means being provided with means for making said signal representative of the initial slope of the signal B at the beginning of its high-slope region, means for periodically comparing said slope with the slope of the signal B, means for generating a second pulse when the slope of the signal B becomes higher than the initial slope measured, and means for measuring the time interval which elapses between the first and the second pulses.

6. A device according to claim 5, wherein said transparency increases as a function of time, wherein the means for generating the signal B comprise means for periodically illuminating said simple, means for collecting the light signal which has passed through said simple, and means for converting said light signal to an electrical signal which is proportional in time to the amplitude of said collected light signal.

7. A device according to claim 5, wherein the transparency of the sample decreases as a function of time, and wherein said device comprises means for generating the signal B including means for periodically illuminating said sample, means for collecting the light signal which has passed through said sample and for converting said light signal to an electrical signal which is proportional in time to the amplitude of said light signal, and means for complementing said signal B to a value which is higher than the maximum value of said signal B.

8. A device according to claim 5, wherein the means for illuminating and collecting the light signal are constituted by an electroluminescent diode which is supplied during finite periods of time, said diode being placed on one side of the sample, and by a phototransistor placed on the other side of the sample and capable of collecting the light signal which has passed through said sample.

9. A device according to claim 5, wherein the means for making the signal A representative of the slope of the signal B comprise means for defining an instant $T_1$ corresponding to the beginning of the high-slope region, means for giving the signal A at said instant $T_1$ a value equal to the value $B_1$ of the signal at said instant and for adding a quantity N to said value $B_1$ in order to ensure that the signal A is of higher value than the signal B at said instant, means for detecting the instant $T_2$ at which the signal B becomes equal to the value $B_1$ + N, and means for measuring the time interval $t$ which elapses between the instants $T_1$ and $T_2$. the ratio $N/t$ being intended to give the value of said slope.

10. A device according to claim 9, wherein the means for defining the instant $T_1$ consist of means for giving the signal A at the initial instant $t_0$ the value $B_0$ which the signal B has at said instant $t_0$ increased by the value N, means for detecting the instant $T_1$ at which the signal B assumes the value $B_0$ + N, means for giving the value $B_0$ + 2N to the signal A at said instant and means for detecting the instant at which the signal B becomes equal to $B_0$ + 2N, said instant being the instant $T_1$.

11. A device according to claim 5, wherein the means for comparing the slope of the signal B at each instant with the slope of the signal B at the beginning of the high-slope zone comprise means for giving the signal A at an instant $T_3$ which is slightly later in time than the instant $T_2$ a value $A_3$ which is slightly lower than the value of the signal B at said instant, means for giving a stairstep wave form to the signal A starting from an instant $T_3$ by adding the value N to the signal at each instant $T_3 + nt$, and means for comparing the value of the signal A with the value of the signal B and for generating said second pulse when the signal A becomes higher in value than the signal B.

* * * * *